US012653844B2

(12) United States Patent
Toda et al.

(10) Patent No.: US 12,653,844 B2
(45) Date of Patent: Jun. 16, 2026

(54) MITOCHONDRIAL FUNCTION-IMPROVING COMPOSITION

(71) Applicant: MORINAGA MILK INDUSTRY CO., LTD., Tokyo (JP)

(72) Inventors: Kazuya Toda, Kanagawa (JP); Shin Yoshimoto, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 567 days.

(21) Appl. No.: 18/001,315

(22) PCT Filed: Jun. 14, 2021

(86) PCT No.: PCT/JP2021/022576
§ 371 (c)(1),
(2) Date: Dec. 9, 2022

(87) PCT Pub. No.: WO2021/251505
PCT Pub. Date: Dec. 16, 2021

(65) Prior Publication Data
US 2023/0248782 A1      Aug. 10, 2023

(30) Foreign Application Priority Data
Jun. 12, 2020      (JP) ................................. 2020-102240

(51) Int. Cl.
*A61K 35/74*      (2015.01)
*A23L 33/135*      (2016.01)
*A61P 21/00*      (2006.01)

(52) U.S. Cl.
CPC ............ *A61K 35/74* (2013.01); *A23L 33/135* (2016.08); *A61P 21/00* (2018.01)

(58) Field of Classification Search
CPC ........ A61K 35/74; A61K 9/0095; A61K 9/08; A61K 35/741; A23L 33/135; A61P 21/00; A61P 29/00; A61P 43/00; C12N 1/20
See application file for complete search history.

(56) References Cited

U.S. PATENT DOCUMENTS

| | | |
|---|---|---|
| 2018/0357375 A1 | 12/2018 | Cutcliffe et al. |
| 2019/0314425 A1 | 10/2019 | Kim et al. |
| 2020/0384037 A1 | 12/2020 | Hsiao et al. |

FOREIGN PATENT DOCUMENTS

| | | | |
|---|---|---|---|
| JP | 2017-031120 A | 2/2017 | |
| JP | 2020-502281 A | 1/2020 | |
| KR | 10-2329853 B1 | 11/2021 | |
| WO | WO-2017060698 A1 * | 4/2017 | ........... A61K 35/741 |
| WO | WO-2019168401 A1 * | 9/2019 | ............ A61K 35/38 |
| WO | WO2019/212997 A1 | 11/2019 | |
| WO | WO2020/058979 A9 | 3/2020 | |

OTHER PUBLICATIONS

Ouwerkerk et al., *Akkermansia glycaniphila* sp. nov., an anaerobic mucin-degrading bacterium isolated from reticulated python faeces, International Journal of Systematic and Evolutionary Microbiology (2016), vol. 66, p. 4614-4620. (Year: 2016).*

Zhao et al., Akkermansia muciniphila improves metabolic profiles by reducing inflammation in chow diet-fed mice, Jour Mol Endocrinol, 58(1), p. 1-14 (Year: 2017).*

International Search Report for PCT Patent App. No. PCT/JP2021/022576 (Jul. 13, 2021).

Gotkine, M., et al., "Amyotrophic lateral sclerosis and intestinal microbiota—toward establishing cause and effect," Gut Microbes 2020;11(6):1833-1841.

Katsyuba, E., et al., "De novo NAD+ synthesis enhances mitochondrial function and improves health," Nature 2018;563(7731):354-359.

Yaku, K., et al., "Regulatory role of NAD metabolism in aging," Biomed. Gerontol. 2017;41(1):23-27, with partial English language translation.

Costmagna, D., et al., "Role of Inflammation in Muscle Homeostasis and Myogenesis," Mediators of Inflammation, Hindawi Publishing Corp., 2015, Article ID 805172, 14 pp.

Perez-Campo, R., et al., "The rate of free radical production as a determinant of the rate of aging: evidence from the comparative approach," J. Comp. Physiol. B. 1998;168:149-158.

Tezze, C., et al., "Age-Associated Loss of OPA1 in Muscle Impacts Muscle Mass, Metabolic Homeostasis, Systemic Inflammation, and Epithelial Senescence," Cell Metabolism 2017;25(6):1374-1389.

Derrien, M., et al., "*Akkermansia muciniphila* gen. nov., sp. nov., a human intestinal mucin-degrading bacterium," International Journal of Systematic and Evolutionary Microbiology 2004;54:1469-1476.

Dao, M. C., et al., "Akkermansia muciniphila and improved metabolic health during a dietary intervention in obesity: relationship with gut microbiome richness and ecology," Gut 2016;65:426-436.

Extended European Search Report for European Patent App. No. 21822998.7 (Nov. 18, 2024).

Blacher, E., et al., "Potential roles of gut microbiome and metabolites in modulating ALS in mice," Nature 2019;572:474-480.

Office Action & Search Report dated Aug. 7, 2025 issued in corresponding CN Patent Application No. 202180041783.6, with English language translation thereof.

Dong, X., et al., "The Role of Acmania in Diabetes and Obesity," Acta Microbiologica Sinica, 2020, 60(5), 856-863, with English language translation thereof.

* cited by examiner

*Primary Examiner* — Robert B Mondesi
*Assistant Examiner* — Naghmeh Nina Moazzami
(74) *Attorney, Agent, or Firm* — Cermak & McGowan LLP; Shelly Guest Cermak

(57)      ABSTRACT

An aspect is to provide an active ingredient which can improve mitochondrial function. Another aspect is to provide a composition for suppressing muscle inflammation or muscular atrophy. One, two, or more kinds selected from a bacterium of the genus *Akkermansia*, a culture of the bacterium and a treated product of the bacterium are used as an active ingredient in a mitochondrial function-improving composition. The composition can be preferably applied for suppressing muscle inflammation or suppressing muscular atrophy.

9 Claims, 1 Drawing Sheet

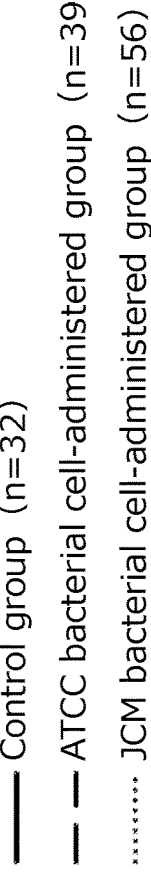
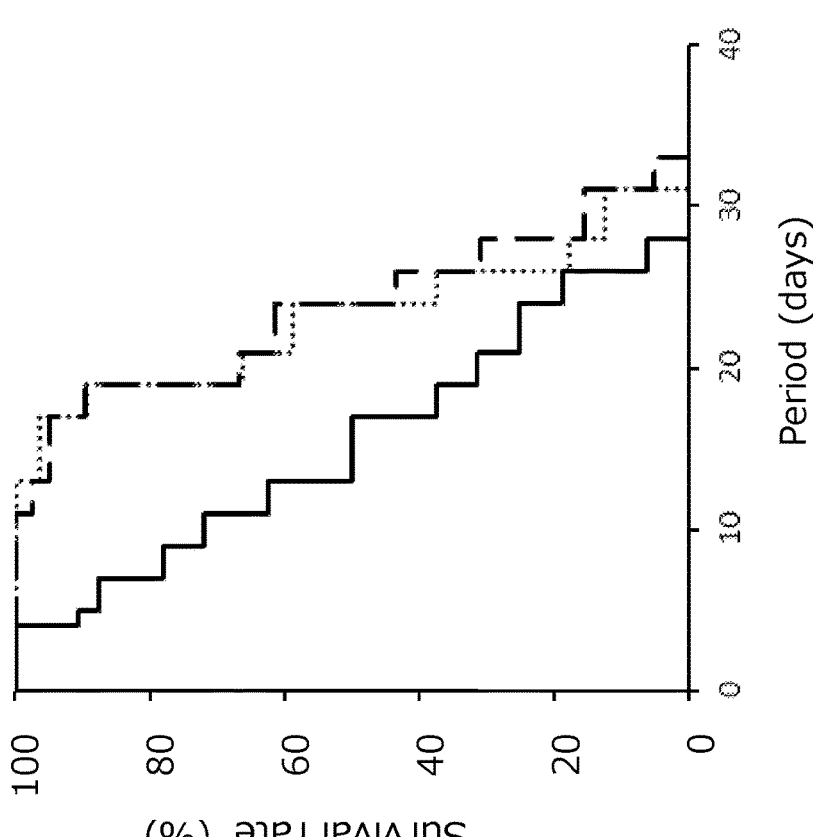

MITOCHONDRIAL FUNCTION-IMPROVING COMPOSITION

The present application is a national phase filing, and claims priority under 35 U.S.C. § 371 to, International Application No. PCT/JP2021/022576, filed Jun. 14, 2021, and claims priority therethrough under 35 U.S.C. § 119 to Japanese Patent Application No. 2020-102240 filed on Jun. 12, 2020 in Japan, and the contents thereof are incorporated here by reference.

TECHNICAL FIELD

The present invention relates to a mitochondrial function-improving composition, a muscle inflammation-suppressing composition and a muscular atrophy-suppressing composition.

BACKGROUND ART

Mitochondria are cell organelles responsible for various functions such as energy production by ATP production.

It is known that when there is mitochondrial dysfunction, reactive oxygen species (ROS), which are by-products of energy metabolism, are produced excessively and cause undesirable phenomena to an individual.

Specifically, reactive oxygen species damage cells and cause inflammation of muscles and the like. Because inflammation of muscles induces promotion of degradation of muscle proteins and myogenetic disorder and promotes a decrease in muscle mass, inflammation of muscles is also one of the causes of muscular atrophy (NPL 1). Muscular atrophy refers to a condition in which the muscle mass decreases due to a decrease in the number of muscle fibers and a decrease in the volume of muscle fibers and is generally accompanied by muscle weakness.

In addition to medical approaches, various proposals for improving inflammation of muscles and muscular atrophy caused therefrom with foods have been recently made (PTL 1 and the like).

It is also known that mitochondrial dysfunction causes aging of an individual. It is proposed that a cause is that the excessively produced free radicals, namely reactive oxygen species, oxidize DNA, proteins, lipids and the like and induce cytotoxicity (NPL 2). In fact, systemic aging symptoms were accelerated in mice in which muscular mitochondrial dysfunction was induced (NPL 3). Moreover, it is believed that an increased dysfunctional mitochondria with aging is one of the factors that cause excessive accumulation of free radicals. Excessive accumulation of free radicals is also well known as one of the stress types that cause cellular senescence.

Accordingly, it is considered that a component which can improve mitochondrial function can be useful for anti-aging.

Here, the genus *Akkermansia* is a new genus of the order *Verrucomicrobiales* proposed in 2004, and *Akkermansia muciniphila*, which is a representative species thereof, is a bacterium which is found in the human intestines and which degrades mucin (NPL 4).

Recently, a relationship between the amount of *Akkermansia muciniphila* in the gut microbiota and obesity and diabetes has been reported (NPL 5).

CITATION LIST

Patent Literature

PTL 1: JP-A-2017-031120

Non Patent Literature

NPL 1: Costamagna, D. et. Al., Mediators Inflamm., 805172 (2015)

NPL 2: R Perez-Campo, M Lopez-Torres, S Cadenas, C Rojas, G Barja. J Comp Physiol B, 168 (3), 149-158 (1998)

NPL 3: Tezze C, Romanello V, Desbats MA Cell Metab. 25 (6): 1374-1389. (2017)

NPL 4: Muriel D. et. al., Int. J. Syst. and Evol. Microbiol., 54:1469-1476. (2004)

NPL 5: Dao MC. et. al., Gut. 65:426-436 (2016)

SUMMARY OF INVENTION

Technical Problem

A problem of the invention is to provide a composition for improving mitochondrial function, a composition for suppressing muscle inflammation and muscular atrophy caused therefrom and an anti-aging composition.

Solution to Problem

As a result of extensive research to solve the problem, the present inventors have found that a bacterium of the genus *Akkermansia* and a culture or a treated product thereof have an effect of improving mitochondrial dysfunction and thus have completed the invention.

That is, an embodiment of the invention is a mitochondrial function-improving composition comprising one, two or more kinds selected from a bacterium of the genus *Akkermansia*, a culture of the bacterium and a treated product of the bacterium.

Another embodiment of the invention is a muscle inflammation-suppressing composition comprising one, two or more kinds selected from a bacterium of the genus *Akkermansia*, a culture of the bacterium and a treated product of the bacterium.

Another embodiment of the invention is a muscular atrophy-suppressing composition comprising one, two or more kinds selected from a bacterium of the genus *Akkermansia*, a culture of the bacterium and a treated product of the bacterium.

In the invention, the bacterium of the genus *Akkermansia* is preferably selected from *Akkermansia muciniphila* and *Akkermansia glycaniphila*.

The composition of the invention is preferably a food or a drink.

The composition of the invention is preferably a pharmaceutical product.

Advantageous Effects of Invention

According to the invention, mitochondrial function can be improved.

Through improvement of mitochondrial function, muscle inflammation can be suppressed, and inflammatory muscular atrophy can also be suppressed. As a result, a decline in motor function due to inflammation or atrophy of muscles can be suppressed.

Through improvement of mitochondrial function, an anti-aging effect can also be obtained. As a result, lifespan can be prolonged, and an age-related decline in motor function can be suppressed.

BRIEF DESCRIPTION OF DRAWINGS

FIG. 1 A graph showing the survival rate of *Caenorhabditis elegans*.

DESCRIPTION OF EMBODIMENTS

Next, the invention is explained in detail. In this regard, however, the invention is not limited to the following embodiments, and changes can be freely made in the scope of the invention.

The composition of the invention comprises one, two or more kinds selected from a bacterium of the genus *Akkermansia*, a culture of the bacterium and a treated product of the bacterium.

The bacterium of the genus *Akkermansia* is not particularly restricted but can be *Akkermansia muciniphila* or *Akkermansia glycaniphila*.

Of these, *Akkermansia muciniphila* is more preferable.

*Akkermansia muciniphila* can be more specifically *Akkermansia muciniphila* strain JCM30893. Strain JCM30893 can be acquired from the Microbe Division in RIKEN BioResource Research Center (JCM).

*Akkermansia muciniphila* strain ATCC BAA-835 can also be used. Strain ATCC BAA-835 can be acquired from American Type Culture Collection (ATCC).

*Akkermansia glycaniphila* can be more specifically *Akkermansia glycaniphila* strain DSM 100705T. Strain DSM 100705T can be acquired from German Collection of Microorganisms and Cell Cultures (DSMZ).

The bacteria specified by the bacterial names exemplified above are not limited to the strains deposited or registered at the certain organizations under the bacterial names themselves (also called "deposited strains" below for the convenience of explanation) but include substantially equivalent strains thereof (also called "derived strains" or "induced strains"). That is, the bacteria are not limited to the strains deposited to the depositaries with the bacterial strain numbers (accession numbers) themselves but include substantially equivalent strains thereof. The "substantially equivalent strains of a deposited strain" of a bacterium are strains which belong to the identical species to that of the deposited strain, have a genome sequence similarity (Average Nucleotide Identity value) of preferably 90.0% or more, more preferably 95.0% or more, further preferably 99.0% identity to the deposited strain and preferably have the identical bacteriological properties to those of the deposited strain. The substantially equivalent strains of a deposited strain of a bacterium may be, for example, strains derived from the deposited strain as the parent strain. The derived strains include a strain bred from the deposited strain and a strain naturally generated from the deposited strain. Breeding methods include modification by the genetic engineering technique and modification by mutagenesis. The mutagenesis includes X-ray irradiation, ultraviolet irradiation and treatment with a mutagen such as N-methyl-N'-nitro-N-nitrosoguanidine, ethyl methanesulfonate and methyl methanesulfonate. The strain naturally generated from the deposited strain is a strain which is naturally generated from the deposited strain during use. Such a strain is a mutant naturally generated during culture of the deposited strain (for example, passaging culture). The derived strains may be constructed with a kind of modification or constructed with two or more kinds of modification.

As the bacterium of the genus *Akkermansia* present in the composition of the invention, a commercial product may be used. Alternatively, one appropriately produced and obtained may be used, and one obtained by culturing the bacterium of the genus *Akkermansia* described above may also be used.

The culture method is not particularly restricted as long as the bacterium of the genus *Akkermansia* can grow. As the culture method, for example, a method which is generally used for culturing the bacterium of the genus *Akkermansia* can be used directly or with appropriate modification. The culture temperature may be, for example, 25 to 50° C. and is preferably 35 to 42° C. The culture can be conducted preferably under anaerobic conditions and can be conducted, for example, while flowing an anaerobic gas such as carbon dioxide. The culture can also be conducted under microaerophilic conditions such as static liquid culture. The culture can be conducted, for example, until the bacterium of the genus *Akkermansia* grows to a desired degree.

The medium used for the culture is not particularly restricted as long as the bacterium of the genus *Akkermansia* can grow. As the medium, for example, a medium which is generally used for culturing the bacterium of the genus *Akkermansia* can be used directly or with appropriate modification. That is, as a carbon source, for example, saccharides such as mucin, galactose, glucose, fructose, mannose, cellobiose, maltose, lactose, sucrose, trehalose, starch, starch hydrolysate and molasses can be used depending on the assimilation properties. As a nitrogen source, for example, ammonia and ammonium salts and nitrates such as ammonium sulfate, ammonium chloride and ammonium nitrate can be used. Moreover, as an inorganic salt, for example, sodium chloride, potassium chloride, potassium phosphate, magnesium sulfate, calcium chloride, calcium nitrate, manganese chloride, ferrous sulfate and the like can be used. Furthermore, organic components such as peptone, soybean powder, a defatted soybean cake, meat extract and yeast extract may also be used. Specific examples of the medium which is generally used for culturing the bacterium of the genus *Akkermansia* include brain heart infusion (BHI) medium, reinforced clostridial medium, MRS medium (de Man, Rogosa, and Sharpe medium), mMRS medium (modified MRS medium), TOSP medium (TOS propionate medium), TOSP Mup medium (TOS propionate mupirocin medium), GAM (Gifu Anaerobic Medium) medium, YCFA (Yeast Extract-casein Hydrolysate Acid) medium and the like.

The form of the bacterium of the genus *Akkermansia* present in the composition of the invention may be any of bacterial cells, a culture of the bacterium and a treated product of the bacterium.

The bacterial cells are generally preferably comprised in the form of comprising living bacterial cells, but are not particularly limited. The bacterial cells may be, for example, living bacterial cells, dead bacterial cells or a mixture of living bacterial cells and dead bacterial cells.

As the culture of the bacterium, for example, the culture obtained through culture may be used directly. Alternatively, a diluted or concentrated culture may be used, or bacterial cells collected from the culture may also be used. Moreover, as the culture, a culture supernatant or a culture fraction may also be used. When a culture supernatant is used, for example, a supernatant of a culture solution obtained by culturing using BHI medium under anaerobic conditions at 37° C. for 16 hours can be preferably used.

As the treated product of the bacterium, crushed, heated or lyophilized bacterial cells or culture, a diluted product thereof, a dried product thereof or a fraction thereof can be used.

The composition of the invention can exhibit an effect of improving mitochondrial function. Here, the "improvement of function" includes prevention, suppression or delay of dysfunction or a decline in function.

The mitochondrial function can be generally determined using the production amount of reactive oxygen species (ROS) or the transmembrane potential caused through energy production as an indicator. Moreover, the mitochondrial function can also be determined using the enzymatic activity of enzyme complexes in the electron transport chain (respiratory chain complexes) involved in ATP production, the mitochondrial oxygen consumption rate (OCR) or the mitochondrial amount as an indicator.

When there is mitochondrial dysfunction, reactive oxygen species (ROS) are excessively produced, resulting in damage to the cells of muscles and the like and causing inflammation. Accordingly, improvement of mitochondrial function can achieve a muscle inflammation-suppressing effect and/or a muscular atrophy-suppressing effect.

Therefore, the composition of the invention can exhibit a muscle inflammation-suppressing effect. The composition can also exhibit a muscular atrophy-suppressing effect, and the muscular atrophy is generally caused by inflammation.

The "suppression" in the present specification includes improvement or relief of a symptom, delay of deterioration or the onset of a symptom and prevention of the onset of a symptom.

The composition of the invention exhibits a muscle inflammation-suppressing effect as described above and thus can be preferably used for prevention, improvement, or treatment of an inflammatory muscle disease such as polymyositis, dermatomyositis, polymyositis, dermatomyositis, antimitochondrial antibody-positive myositis, inclusion body myositis, necrotizing autoimmune myositis, myocarditis and pericarditis.

Moreover, the composition of the invention exhibits a muscular atrophy-suppressing effect as described above and thus can be preferably used for suppressing a decline in motor function caused by muscular atrophy. The composition can also be preferably used for prevention, improvement, or treatment of a disease showing a muscular atrophy symptom such as sarcopenia, frailty, muscular dystrophy, and myopathy.

When there is mitochondrial dysfunction, reactive oxygen species (ROS) are excessively produced, resulting in damage to cells and promotion of aging. Therefore, improvement of mitochondrial function can achieve an anti-aging effect.

Therefore, the composition of the invention can exhibit an anti-aging effect. The "anti-aging" means to prevent or suppress an age-related change, generally an unfavorable change, or to delay progress thereof.

The composition of the invention exhibits an anti-aging effect as described above and thus can be preferably used for prolonging lifespan or suppressing a decline in motor function. Here, the prolongment of lifespan may include extension of healthy lifespan in addition to simply living long.

Another aspect of the invention is use of one, two, or more kinds selected from a bacterium of the genus *Akkermansia*, a culture of the bacterium and a treated product of the bacterium in the manufacture of a mitochondrial function-improving composition.

Another aspect of the invention is use of one, two, or more kinds selected from a bacterium of the genus *Akkermansia*, a culture of the bacterium and a treated product of the bacterium in the improvement of mitochondrial function.

Another aspect of the invention is one, two, or more kinds selected from a bacterium of the genus *Akkermansia*, a culture of the bacterium and a treated product of the bacterium which is used for improving mitochondrial function.

Another aspect of the invention is a method of improving mitochondrial function including administering one, two, or more kinds selected from a bacterium of the genus *Akkermansia*, a culture of the bacterium and a treated product of the bacterium to a subject.

Another aspect of the invention is use of one, two, or more kinds selected from a bacterium of the genus *Akkermansia*, a culture of the bacterium and a treated product of the bacterium in the manufacture of a muscle inflammation-suppressing composition.

Another aspect of the invention is use of one, two, or more kinds selected from a bacterium of the genus *Akkermansia*, a culture of the bacterium and a treated product of the bacterium in the suppression of muscle inflammation.

Another aspect of the invention is one, two, or more kinds selected from a bacterium of the genus *Akkermansia*, a culture of the bacterium and a treated product of the bacterium which is used for suppressing muscle inflammation.

Another aspect of the invention is a method of suppressing muscle inflammation including administering one, two or more kinds selected from a bacterium of the genus *Akkermansia*, a culture of the bacterium and a treated product of the bacterium to a subject.

Another aspect of the invention is use of one, two, or more kinds selected from a bacterium of the genus *Akkermansia*, a culture of the bacterium and a treated product of the bacterium in the manufacture of a muscular atrophy-suppressing composition.

Another aspect of the invention is use of one, two, or more kinds selected from a bacterium of the genus *Akkermansia*, a culture of the bacterium and a treated product of the bacterium in the suppression of muscular atrophy.

Another aspect of the invention is one, two, or more kinds selected from a bacterium of the genus *Akkermansia*, a culture of the bacterium and a treated product of the bacterium which is used for suppressing muscular atrophy.

Another aspect of the invention is a method of suppressing muscular atrophy including administering one, two or more kinds selected from a bacterium of the genus *Akkermansia*, a culture of the bacterium and a treated product of the bacterium to a subject.

The subject to which the composition of the invention is administered (subject of administration) and the subject which takes the composition (subject of intake) are not particularly limited as long as the subjects are animals, but are generally humans. Moreover, the subjects may be an adult, a child, an infant, a newborn (including an underweight infant) and the like but are generally adults. The gender thereof is not particularly limited.

The bacterium of the genus *Akkermansia* of the invention may be used for therapeutic purpose or may be used for non-therapeutic purpose. That is, the mitochondrial function-improving effect, the muscle inflammation-suppressing effect, the muscular atrophy-suppressing effect or the anti-aging effect may be obtained for therapeutic purpose or may be obtained for non-therapeutic purpose unless otherwise specified.

The "therapeutic purpose" may mean, for example, a concept including medical purpose and may specifically mean a concept including treatment of a human body by therapy.

The "non-therapeutic purpose" may mean, for example, a concept which does not include medical purpose and may specifically mean a concept which does not include treatment of a human body by therapy. The non-therapeutic purpose can be health promotion purpose or beauty purpose.

The "prevention of a symptom or a disease" may mean, for example, prevention and/or delay of the onset of the symptom or the disease or a decrease in the possibility of the onset of the symptom or the disease. The "improvement of a symptom or a disease" or the "treatment of a symptom or a disease" may mean, for example, improvement of the symptom or the disease, prevention or delay of deterioration of the symptom or the disease or prevention or delay of progress of the symptom or the disease. The "improvement of a symptom or a disease" may specifically mean any of the events which can be obtained for non-therapeutic purpose. The "treatment of a symptom or a disease" may specifically mean any of the events which can be obtained for therapeutic purpose.

The amount of the bacterium of the genus *Akkermansia* present in the composition of the invention may be set, for example, in such a manner that the dosage of the active ingredient mentioned in the method of the invention is achieved.

The form of the composition of the invention is not particularly restricted. As the form of the composition of the invention, an acceptable form can be used depending on the use form of the composition of the invention. The form of the composition of the invention can be specifically any of the forms exemplified for the food or drink composition, the pharmaceutical composition or the feed composition described below. The amount may be set, for example, in such a manner that the dosage of the active ingredient mentioned in the method of the invention is achieved.

The form of the composition of the invention is not particularly restricted. As the form of the composition of the invention, an acceptable form can be used depending on the intended use of the composition of the invention. The form of the composition of the invention can be specifically any of the forms exemplified as the food or drink composition, the pharmaceutical composition, or the feed composition described below.

In the present specification, "administering one, two, or more kinds selected from a bacterium of the genus *Akkermansia*, a culture of the bacterium and a treated product of the bacterium to an animal" may be synonymous with "causing an animal to take one, two, or more kinds selected from a bacterium of the genus *Akkermansia*, a culture of the bacterium, and a treated product of the bacterium". The intake is generally voluntary (free intake) but may be forced (forced intake). That is, the administration step may be specifically, for example, a step of blending one, two, or more kinds selected from a bacterium of the genus *Akkermansia*, a culture of the bacterium and a treated product of the bacterium in a food, a drink or feed for supplying to the subject and thus causing the subject to freely take the food, the drink, or the feed.

The timing of intake (administration) of the composition of the invention is not particularly limited and can be appropriately selected depending on the condition of the subject of intake (administration).

The intake (dosage) of the composition of the invention is appropriately selected based on the age of the subject of intake (administration), the gender, the condition, other conditions, and the like.

The intake (dosage) of the composition of the invention, as the intake (dosage) of the bacterial cells of the bacterium of the genus *Akkermansia* according to the invention, is, for example, preferably in the range of 0.5 to 5 g/day for an adult, more preferably in the range of 1 to 4 g/day, further preferably 2 to 3 g/day. Alternatively, the intake (dosage) of a culture supernatant of the bacterium of the genus *Akkermansia* is, for example, preferably in the range of 0.5 to 5 g/day for an adult, more preferably in the range of 1 to 4 g/day, further preferably 2 to 3 g/day.

Regardless of the amount or the period of intake (administration), the composition of the invention can be taken (administered) once a day or in multiple divided portions.

The amount of the bacterium of the genus *Akkermansia*, the culture of the bacterium or the treated product of the bacterium comprised in the composition of the invention may be, for example, as the bacterial amount of the bacterium, $1 \times 10^4$ cells/g or more, $1 \times 10^5$ cells/g or more, $1 \times 10^6$ cells/g or more, $1 \times 10^7$ cells/g or more or $1 \times 10^8$ cells/g or more, may be $1 \times 10^{13}$ cells/g or less, $1 \times 10^{12}$ cells/g or less or $1 \times 10^{11}$ cells/g or less and may be in the range of a combination thereof. The amount of the bacterium of the genus *Akkermansia*, the culture of the bacterium, or the treated product of the bacterium present in the composition of the invention may be, for example, as the bacterial amount of the bacterium, $1 \times 10^4$ cells/mL or more, $1 \times 10^5$ cells/mL or more, $1 \times 10^6$ cells/mL or more, $1 \times 10^7$ cells/mL or more or $1 \times 10^8$ cells/mL or more, may be $1 \times 10^{13}$ cells/mL or less, $1 \times 10^{12}$ cells/mL or less or $1 \times 10^{11}$ cells/mL or less and may be in the range of a combination thereof. The amount of the bacterium of the genus *Akkermansia*, the culture of the bacterium or the treated product of the bacterium present in the composition of the invention may be specifically, as the bacterial amount of the bacterium, $1 \times 10^4$ to $1 \times 10^{13}$ cells/g, $1 \times 10^5$ to $1 \times 10^{13}$ cells/g, $1 \times 10^6$ to $1 \times 10^{12}$ cells/g, preferably $1 \times 10^7$ to $1 \times 10^{11}$ cells/g, more preferably $1 \times 10^8$ to $1 \times 10^{10}$ cells/g. The amount of the bacterium of the genus *Akkermansia*, the culture of the bacterium or the treated product of the bacterium present in the composition of the invention may be specifically, as the bacterial amount of the bacterium, $1 \times 10^4$ to $1 \times 10^{13}$ cells/mL, $1 \times 10^5$ to $1 \times 10^{13}$ cells/mL, $1 \times 10^6$ to $1 \times 10^{12}$ cells/mL, preferably $1 \times 10^7$ to $1 \times 10^{11}$ cells/mL, more preferably $1 \times 10^8$ to $1 \times 10^{10}$ cells/mL.

When the bacterial cells are living cells, the cells can be replaced with CFU. In this regard, the "CFU" refers to colony forming unit. In the present specification, for example, a value obtained by culturing on a solid medium having 10 mass % reduced skim milk powder at 38° C. can be used.

When a culture supernatant is used as the culture of the bacterium, the amount as the solid content is preferably 0.1 to 100 mass % of the entire composition and can be more preferably 1 to 90 mass %, further preferably 10 to 80 mass %.

The ranges may be generally ranges of amount for distribution as an oral composition.

The period of intake (administration) of the composition of the invention is not particularly limited. The upper limit of the period of intake (administration) is not particularly set, and continuous long-term intake (administration) is possible.

The route of intake (administration) of the composition of the invention may be an oral or parenteral route but is preferably an oral route. The parenteral intake (administration) is transdermal, intravenous or rectal administration, inhalation or the like.

When the composition of the invention is an orally taken (administered) composition, the composition is preferably a food or a drink in an embodiment.

The form and the property of the food or the drink are not particularly restricted as long as the food or the drink does not impair the effects of the invention and can be orally taken (administered), and the food or the drink can be produced by a general method using a material which is generally used for a food or a drink except that one, two or more kinds selected from a bacterium of the genus *Akkermansia*, a culture of the bacterium and a treated product of the bacterium are included.

The food or the drink is not limited regarding the form, such as liquid, paste, gel solid or powder. Examples include the following examples: nutritional supplements (supplements), tablet candies; liquid foods (nutrition products for tube feeding); wheat products such as breads, macaroni, spaghetti, noodles, cake mixes, frying flours and bread crumbs; instant foods such as instant noodles, cup noodles, retort-pouched/prepared foods, prepared canned foods, microwave foods, instant soups/stews, instant miso soups/clear Japanese soups, canned soups, freeze-dried foods and other instant foods; processed agricultural products such as canned agricultural products, canned fruits, jams/marmalades, pickles, cooked beans, dried agricultural products and cereals (processed grains); processed fishery products such as canned fishery products, fish hams/sausages, fishery paste products, fishery delicacies and Tsukudani (foods boiled down in sweetened soy sauce); processed livestock products such as canned livestock products/pastes and livestock hams/sausages; milk/dairy products such as processed milk, milk beverages, yogurts, lactic acid bacteria beverages, cheeses, ice creams, powdered formula, creams and other dairy products; oils and fats such as butter, margarine and vegetable oils; basic condiments such as soy sauce, soybean paste, sauces, processed tomato condiments, Mirin (sweet sake for seasoning) and vinegars; compound flavor enhancers/foods such as cooking mixes, curry roux, sauces, dressings, noodle broths, spices and other compound flavor enhancers; frozen foods such as frozen food materials, semi-cooked frozen foods and cooked frozen foods; confectioneries such as caramels, candies, chewing gums, chocolates, cookies, biscuits, cakes, pies, snacks, crackers, Japanese-style confectioneries, rice confectioneries, bean confectioneries, desserts, jellies and other confectioneries; luxury beverages such as carbonated drinks, natural juices, fruit juices, fruit juice-comprising soft drinks, fruit flesh drinks, fruit granule-comprising fruit juices, vegetable drinks, soy milk, soy milk drinks, coffee drinks, tea drinks, drink powders, concentrated drinks, sport drinks, nutritional drinks, alcohols and other luxury beverages, other commercial foods such as baby foods, Furikake (dry Japanese seasonings) and seasonings for Chazuke (boiled rice with hot tea) and the like; powdered infant formula; enteral nutrition products; food with health claims (foods for specified health uses, foods with nutrient function claims and foods with functional claims), nutritional supplements and the like.

An embodiment of the food or the drink can be feed. The feed is pet food, livestock feed, fish farming feed, or the like.

The form of the feed is not particularly restricted, and the feed may comprises, in addition to one, two, or more kinds selected from a bacterium of the genus *Akkermansia*, a culture of the bacterium and a treated product of the bacterium, for example: grain such as corn, wheat, barley, rye and milo; vegetable oil cake such as soybean oil cake, rapeseed oil cake, coconut oil cake and linseed oil cake; bran such as oat bran, wheat bran, rice bran and defatted rice bran; a food manufacturer's by-product such as corn gluten meal and corn jam meal; animal feed such as fish powder, skim milk powder, casein, yellow grease and tallow; yeast such as torula yeast and brewer's yeast; mineral feed such as tertiary calcium phosphate and calcium carbonate; an oil or a fat; a single amino acid; a saccharide; or the like.

When the composition of the invention is an embodiment of a food or a drink (including feed), the composition can be provided/sold as a food or a drink labeled with use related to improvement of mitochondrial function, suppression of muscle inflammation, suppression of muscular atrophy and/or anti-aging.

The "labeling" act includes all the acts for informing a consumer of the use, and all the expressions which can remind of/cause to guess the use are the "labeling" acts of the invention, regardless of the purposes of labeling, the contents of labeling, the objects to be labeled, the media and the like.

The "label" is preferably with an expression which allows a consumer to directly recognize the use. Specific examples include an act of transferring an article in which the use is described on a product regarding the food or the drink or packaging of a product, delivering such an article, displaying such an article for transfer or delivery or importing such an article, an act of displaying or distributing an advertisement of a product, a price list or a business document with a description of the use thereon or providing information with such contents with a description of the use by an electromagnetic method (internet or the like) and another act.

The content of the label is preferably a label approved by the administration or the like (for example, a label approved based on a system provided by the administration and provided in the form based on the approval or the like). It is preferable to label with such a content on packaging, a compriser, a catalogue, a brochure, an advertisement material in a sales site such as POP, other documents or the like.

The "labels" also include labels with health foods, functional foods, enteral nutrition products, food for special dietary uses, food with health claims, foods for specified health uses, foods with nutrient function claims, foods with function claims, quasi-drugs, and the like. In particular, the labels are labels approved by the Consumer Affairs Agency, such as labels approved by the systems for foods for specified health uses, foods with nutrient function claims or foods with function claims or by a similar system and the like. Specific examples include a label with foods for specified health uses, a label with qualified foods for specified health uses, a label indicating influence on the structure or the function of a body, a label with reduction of disease risk, a label with a scientifically grounded function, and the like. More specifically, typical examples include labels with food for specified health uses (especially labels with health uses) provided by the Cabinet Office Ordinance on Labeling Permission for Special Dietary Uses under the Health Promotion Act (Cabinet Office Ordinance No. 57 on Aug. 31, 2009) and similar labels.

The labels are, for example, labels such as "for improving energy metabolism", "for maintaining muscles/muscle strength", "for those who are concerned about muscle mass", "for those who are concerned about muscle strength", "for suppressing inflammation of muscles", "for those with atrophy of muscles", "for improving motor function", "for those who wish to prevent aging", "for those who are concerned about an age-related decline in muscles", "for those who are concerned about strength for walking", "for those who wish to prolong healthy lifespan", "for those who are concerned about an age-related decline in walking function", "for those who are concerned about physical deterioration", and the like.

In an embodiment, the composition of the invention can be a pharmaceutical product.

That is, the composition of the invention can be a composition for preventing, improving and/or treating a symptom, or a disease related to mitochondrial dysfunction or a decline in mitochondrial function comprising one, two, or more kinds selected from a bacterium of the genus *Akkermansia*, a culture of the bacterium and a treated product of the bacterium.

The composition of the invention can also be a composition for preventing, improving, and/or treating a symptom or a disease related to muscle inflammation comprising one, two, or more kinds selected from a bacterium of the genus *Akkermansia*, a culture of the bacterium and a treated product of the bacterium. Here, symptoms or diseases related to muscle inflammation include polymyositis, dermatomyositis, antimitochondrial antibody-positive myositis, inclusion body myositis, necrotizing autoimmune myositis, myocarditis, pericarditis and the like.

The composition of the invention can also be a composition for preventing, improving and/or treating a symptom, or a disease related to muscular atrophy comprising one, two or more kinds selected from a bacterium of the genus *Akkermansia*, a culture of the bacterium and a treated product of the bacterium. Here, diseases related to muscular atrophy include sarcopenia, frailty, muscular dystrophy, myopathy, and the like.

Regarding the form of the pharmaceutical product, the composition can be appropriately formulated into a desired dosage form depending on the intake (administration) method. For example, in the case of oral intake (administration), the composition can be formulated into a solid preparation such as powder, granules, tablets and capsules, a liquid preparation such as a solution, a syrup, a suspension, and an emulsion, or the like. In the case of parenteral intake (administration), the composition can be formulated into a suppository, ointment, an injection or the like.

For the formulation, a component which is generally used for formulation such as excipients, pH-adjusting agents, colorants and corrigents can be used. Another medicinal component or another medicine such as a component having a mitochondrial function-improving effect, a muscle inflammation-suppressing effect, a muscular atrophy-suppressing effect or an anti-aging effect which is known or will be found in the future can also be used in combination.

In addition, the formulation can be appropriately conducted by a known method depending on the dosage form. For the formulation, a carrier which is generally used for formulation may be appropriately blended and formulated. Such carriers are excipients, binders, disintegrating agents, lubricants, stabilizers, flavoring agents, and the like.

Examples of the excipients include: saccharide derivatives such as lactose, sucrose, glucose, mannitol and sorbitol; starch derivatives such as cornstarch, potato starch, α-starch, dextrin and carboxymethyl starch; cellulose derivatives such as crystalline cellulose, hydroxypropyl cellulose, hydroxypropyl methylcellulose, carboxymethylcellulose and carboxymethyl cellulose calcium; gum arabic; dextran; pullulan; silicate derivatives such as light silicic anhydride, synthetic aluminum silicate, and magnesium aluminometasilicate; phosphate derivatives such as calcium phosphate; carbonate derivatives such as calcium carbonate; sulfate derivatives such as calcium sulfate; and the like.

Examples of the binders include, in addition to the excipients, gelatin, polyvinylpyrrolidone, macrogol and the like.

Examples of the disintegrating agents include, in addition to the excipients, chemically modified starch or cellulose derivatives such as croscarmellose sodium, sodium carboxymethyl starch and cross-linked polyvinylpyrrolidone and the like.

Examples of the lubricants include: talc; stearic acid; metal stearates such as calcium stearate and magnesium stearate; colloidal silica; waxes such as peegum and spermaceti wax; boric acid; glycols; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acid such as silicic anhydride, and silicic acid hydrate; starch derivatives; and the like.

Examples of the stabilizers include: paraoxybenzoate esters such as methylparaben and propylparaben; alcohols such as chlorobutanol, benzyl alcohol and phenylethyl alcohol; benzalkonium chloride; acetic anhydride; sorbic acid; and the like.

Examples of the flavoring agents include sweeteners, acidulants, aromas, and the like.

In this regard, the carriers used in the case of a liquid preparation for oral intake (administration) include solvents such as water and the like.

The timing for taking (administering) the pharmaceutical product of the invention is not particularly limited, and examples include before a meal, after a meal, between meals, before bedtime, and the like.

EXAMPLES

The invention is explained further specifically below using Examples, but the invention is not limited to the Examples.

[Example 1] Preparation of Bacterial Cells and Culture Supernatant of *Akkermansia muciniphila*

*Akkermansia muciniphila* JCM30893 obtained from the Microbe Division in RIKEN was cultured under anaerobic conditions at 37° C. using BHI medium (manufactured by Becton, Dickinson and Company). After 16 hours of culture, the culture supernatant and the bacterial cells were each collected by centrifugation. The culture supernatant and the bacterial cells are called "JCM supernatant" and "JCM bacterial cells", respectively, below.

*Akkermansia muciniphila* ATCC BAA-835 obtained from ATCC was cultured under anaerobic conditions at 37° C. using L-cysteine-comprising BHI medium. After 16 hours of culture, the culture supernatant and the bacterial cells were each collected by centrifugation. The culture supernatant and the bacterial cells are called "ATCC supernatant" and "ATCC bacterial cells", respectively, below.

[Test Example 1] Examination 1 of Muscle Inflammation-Suppressing Effect in Cells (1) Cell Culture The JCM supernatant prepared in Example 1 or the preculture medium was adjusted to pH7.0±0.1 using an aqueous sodium hydroxide solution and sterilized by filtration.

Mouse myoblast strain C2C12 cells (called mouse myoblasts below) were inoculated to a 12-well plate at $1.5 \times 10^4$ cells/cm² and cultured at 37° C. in 5% $CO_2$ for 24 hours with 10% Fetal Bovine Serum- and 1% Penicillin Streptomycin-comprising DMEM medium (growth medium). Then, the JCM supernatant or the preculture medium sterilized above was added at 1% (v/v) to 2% Horse Serum- and 1% Penicillin Streptomycin-comprising DMEM medium (differentiation induction medium). The group to which the preculture medium was added was used as the control group, and the supernatant after the culture was used as the JCM supernatant-treated group. After further culturing at 37° C. in 5% $CO_2$ for seven days, lipopolysaccharide (LPS) (a final concentration of 10 μg/mL) was added to induce muscle inflammation. As a control without induction of inflammation, a group to which PBS was added instead of LPS was also prepared. Then, the cells were further cultured for 24 hours.

(2) Quantification of Expression of Inflammatory Mediator Gene

The total RNA was collected from the cells after the 24-hour culture using TRIZOL Reagent (Invitrogen), and the expression levels of IL-6, which is an inflammatory mediator, and GAPDH as an internal control gene were quantitatively analyzed using the real-time PCR method. The expression levels of IL-6 were corrected using the expression levels of GAPDH.

(3) Results

The expression levels of IL-6 in the mouse myoblasts are shown in Table 1. The expression level of IL-6 increased through the induction of inflammation by the addition of LPS, and the LPS-induced promotion of the IL-6 expression was suppressed by the JCM supernatant. Specifically, it was observed that, while the expression level increased 10.6-fold compared to the control through the LPS treatment, the increase was suppressed to 6.5 times in the JCM supernatant treated group. The results suggest that the JCM supernatant treatment suppresses muscle inflammation.

TABLE 1

| Improvement Effect on Promotion of Inflammatory Mediator Gene Expression after Muscle inflammation Induction | | |
|---|---|---|
| Sample | LPS Treatment | Average ± Standard Error |
| Control Group (n = 4) | – | 1.00 ± 0.09 |
| | + | 10.62 ± 0.25 |
| JCM Supernatant- | – | 1.13 ± 0.30 |
| Treated Group (n = 4) | + | 6.51 ± 0.52 |

[Test Example 2] Examination 2 of Muscle Inflammation-Suppressing Effect in Cells (1) Cell Culture The cells were cultured in the same manner as that in Test Example 1 (1).

(2) Measurement of Reactive Oxygen Species (ROS) Production Amount

H2DCFDA (manufactured by Cayman Chemical Company) was added at a final concentration of 500 μM to the media after the 24-hour culture, and the cells were cultured for two hours. After the culture, the cells were solubilized with RIPA buffer (manufactured by CST), and lysates were obtained. The fluorescence intensities (Ex: 480 nm/Em: 530 nm) of the obtained lysates were measured using a plate reader. Moreover, the protein concentrations of the lysates were measured by the BCA method, and the fluorescence intensities were corrected using the protein concentrations and used as the ROS production amounts.

(3) Results

The ROS production amounts in the mouse myoblasts are shown in Table 2. The ROS production amount increased through the induction of inflammation by the addition of LPS, and the ROS production was suppressed by the JCM supernatant. Specifically, while ROS were produced also in the myoblasts under the normal conditions without the LPS treatment, the production was suppressed to 0.73 times the amount of the control through the JCM supernatant treatment. Moreover, while the ROS production amount increased 1.35-fold compared to the control in the myoblasts in which inflammation was induced by the LPS treatment, the production was suppressed to 0.84 times in the JCM supernatant-treated group.

ROS are known to induce inflammation of muscles, and it is speculated that suppression of ROS production suppresses muscle inflammation. Because it is known that, in general, ROS are produced excessively when there is mitochondrial dysfunction, the above results are believed to suggest that the culture supernatant of *Akkermansia muciniphila* suppresses the ROS production through improvement of the mitochondrial dysfunction and as a result suppresses muscle inflammation.

TABLE 2

| Improvement Effect on ROS Production under Normal Conditions (without LPS Treatment) | | |
|---|---|---|
| Sample | Normal Conditions (Without LPS Treatment) | Inflammation Induction (With LPS Treatment ) |
| Control Group (n = 8) | 1.00 ± 0.04 | 1.35 ± 0.05 |
| JCM Supernatant-Treated Group (n =8) | 0.73 ± 0.01 | 0.84 ± 0.02 |

Each value is the average ± standard error of the ROS production amount.

[Test Example 3] Examination 3 of Muscle Inflammation-Suppressing Effect in Cells (1) Cell Culture The JCM supernatant or the ATCC supernatant prepared in Example 1 or the preculture medium was adjusted to pH7.0±0.1 using an aqueous sodium hydroxide solution and sterilized by filtration.

Rat myoblast strain L6 cells (called rat myoblasts below) were inoculated to a 12-well plate at $1.5 \times 10^4$ cells/cm$^2$ and cultured at 37° C. in 5% $CO_2$ for 24 hours with 10% Fetal Bovine Serum- and 1% Penicillin Streptomycin-comprising DMEM medium (growth medium). Then, the JCM supernatant, the ATCC supernatant or the preculture medium sterilized above was added at 1% (v/v) to 2% Horse Serum- and 1% Penicillin Streptomycin-comprising DMEM medium (differentiation induction medium). The group to which the preculture medium was added was used as the control group, and the groups to which the culture supernatants were added were used as the supernatant-treated groups. After further culturing at 37° C. in 5% $CO_2$ for seven days, dexamethasone (a final concentration of 100 μM), which is a muscular atrophy inducer, was added. As a control without the induction of muscular atrophy, a group to which PBS was added instead of dexamethasone was also prepared. Then, the cells were further cultured for 24 hours.

(2) Quantification of Expression of Muscular Atrophy-Related Genes

The total RNA was collected from the cells after the 24-hour culture using TRIZOL Reagent (Invitrogen), and the expression levels of Atrogin-1 and MuRF-1, which are muscular atrophy-related genes, and GAPDH as an internal control gene were quantitatively analyzed using the real-time PCR method. The expression level of each gene was corrected using the expression level of GAPDH.

(3) Results

The expression levels of Atrogin-1 and MuRF-1 in the rat myoblasts are shown in Table 3. While the expression levels of Atrogin-1 and MuRF-1 increased through the induction of muscular atrophy by the addition of dexamethasone, the dexamethasone-induced promotion of Atrogin-1 and MuRF-1 expression was suppressed by the addition of the culture supernatants.

TABLE 3

Improvement Effect on Promotion of Muscular Atrophy-Related Gene Expression after Muscular Atrophy Induction

| Gene Name | Bacterial Strain | Super-natant Treatment | Normal Conditions (Without Dexamethasone Treatment) | Muscular Atrophy Induction (With Dexamethasone Treatment) |
|---|---|---|---|---|
| Atrogin-1/ | ATCC | − | 1.00 ± 0.07 | 16.51 ± 2.92 |
| GAPDH | | + | 1.01 ± 0.07 | 12.81 ± 2.03 |
| | JCM | − | 1.00 ± 0.14 | 13.57 ± 0.81 |
| | | + | 0.93 ± 0.10 | 10.20 ± 0.90 |
| MuRF-1/ | ATCC | − | 1.00 ± 0.09 | 10.04 ± 1.67 |
| GAPDH | | + | 0.92 ± 0.07 | 6.33 ± 0.90 |
| | JCM | − | 1.00 ± 0.12 | 7.99 ± 0.90 |
| | | + | 0.76 ± 0.06 | 5.99 ± 0.52 |

In each group, n = 4, and each value is the average ± standard error of the relative expression level.

[Test Example 4] Examination of Motor Function-Improving Effect in Nematodes in Aged Stage (1) Nematode Culture Nematodes (*Caenorhabditis elegans*, strain N2) and *Escherichia coli* OP50 (OP50 below) as the feed thereof were obtained from *CAENORHABDITIS* GENETICS CENTER.

OP50 was cultured under aerobic conditions at 37° C. using LB medium (manufactured by Becton, Dickinson and Company). After 16 hours of culture, the bacterial cells of OP50 were collected by centrifugation. The obtained bacterial cells of OP50 were smeared on NGM plates (OP50 bacterial cells 300 mg/plate) and used for culturing nematodes. The other procedures regarding the reagents, nematode culture and synchronization were conducted in accordance with the reference documents below.

Reference Documents

S. Brenner, Genetics, 77 (1), 71-94, 1974, The Genetics of *Caenorhabditis Elegans*
F. Amrit, et. Al., Methods, 68 (3), 465-475, 2014, The *C. elegans* lifespan assay toolkit (2) Preparation of Test Plates 2'-Deoxy-5-fluorouridine (manufactured by Tokyo Chemical Industry Co., Ltd.) was added to the OP50-smeared NGM plates to obtain control plates (control group). In this regard, 2'-deoxy-5-fluorouridine was added to prevent hatching of new individuals. Test product plates (JCM bacterial cell-administered group) were prepared from the control plates by replacing a half of the amount of normal OP50 feed with the JCM bacterial cells of *Akkermansia muciniphila* prepared in Example 1.

(3) Assessment of Motor Function

Synchronized nematodes (L4/adult stage) were cultured on the control plates or the test product plates by adding the normal feed or the JCM bacterial cells. The nematodes cultured for 7 days (young stage) or 14 days (aged stage) were picked with platinum loops and moved into M9 buffer, and the numbers of crawling movements were counted for 30 seconds under a microscope. The measurement was made per individual.

(4) Results

The numbers of 30-second crawling movements of the nematodes in the young stage and the aged stage are shown in Table 4. While the number of the young stage was 36.7, the number of the aged stage of the control group decreased to 24.5. As compared to the control, the number of the test product-treated group was 36.2. Although the muscles of nematodes in the aged stage are generally contracted and the motor function declines compared to the young stage, the decline in function was improved by the administration of the JCM bacterial cells. It was speculated to be because the JCM bacterial cells exhibited a muscular atrophy-suppressing effect through the improvement of mitochondrial function.

TABLE 4

Motor Function-Improving Effect in Nematodes in Aged Stage

| | Number of Crawling Movements |
|---|---|
| young (n = 9) Stage | 36.7 ± 4.4 |
| Aged Control Group (n = 12) Stage | 24.5 ± 6.9 |
| JCM Bacterial Cell-Administered Group (n = 13) | 36.2 ± 6.1 |

Each value is the average ± standard error during 30 seconds.

[Test Example 5] Examination 1 of Improvement Effect on Mitochondrial Dysfunction in Nematodes in Aged Stage (1) Nematode Culture and Preparation of Test Plates The nematode culture and the preparation of test plates were conducted in the same manners as those in Test Example 4 (1).

(2) Measurement of ROS Production Amount

Nematodes in the aged stage which were cultured for 14 days on the control plates or the test product plates were suspended in M9 buffer, inoculated to a 96-well plate and cultured for three hours after adding H2DCFDA (a final concentration of 500 μM). Then, the production amounts of reactive oxygen species (ROS) were quantified by measuring the fluorescence intensities (Ex: 480 nm/Em: 530 nm) using a plate reader, and the nematode number in each well was counted under a microscope and used for correction.

(3) Results

The ROS production amounts in the nematodes in the aged stage are shown in Table 5. The ROS production was suppressed by the administration of the JCM bacterial cells. Specifically, it was observed that the production was suppressed to 0.30 times the amount of the control in the JCM bacterial cell-administered group. While the mitochondrial function is generally abnormal or declines in nematodes in the aged stage, it was observed that the function improves by the administration of the JCM bacterial cells.

17 18

TABLE 5

Improvement Effect on Age-Related Mitochondrial
Dysfunction (ROS Production)

| | Fluorescence Intensity/ Number of Individuals |
|---|---|
| Control Group (n = 10) | 1.000 ± 0.013 |
| JCM Bacterial Cell-Administered Group (n = 10) | 0.297 ± 0.006 |

Each value is the average ± standard error.

[Test Example 6] Examination 2 of Improvement Effect on Mitochondrial Dysfunction in Nematodes in Aged Stage (1) Nematode Culture and Preparation of Test Plates The nematode culture and the preparation of test plates were conducted in the same manners as those in Test Example 4 (1).

(2) Measurement of Mitochondrial Membrane Potential

Nematodes in the aged stage which were cultured for 14 days on the control plates or the test product plates were suspended in M9 buffer, inoculated to a 96-well plate and cultured for 30 minutes after adding JC-1 manufactured by Dojindo Laboratories (a final concentration of 10 μM). Then, the membrane potentials were quantified by measuring the fluorescence intensities (Red: Ex 550 nm, Em 600 nm, Green: Ex 485 nm, Em 535 nm) using a plate reader.

When mitochondria function is normal and when the transmembrane potential is maintained, JC-1 aggregates and emits red fluorescence. When the membrane potential decreases, however, JC-1 exists as a monomer and emits green fluorescence. The change between the intensities of red fluorescence and green fluorescence corresponds to the change in the membrane potential caused by the energy production in mitochondria, and thus the energy production function, which is one of the mitochondrial functions, can be assessed by the method (see WaKo Bio Window September 2019/No. 161, p.27).

(3) Results

The fluorescence intensity ratios (red/green) due to JC-1 in the nematodes in the aged stage are shown in Table 6. The fluorescence intensity ratio was increased by the administration of the JCM bacterial cells. Specifically, it was observed that the ratio increased 1.78-fold compared to the control in the JCM bacterial cell-administered group. This suggests that the mitochondrial function (energy production) was improved by the administration of the JCM bacterial cells.

TABLE 6

Improvement Effect on Age-Related Mitochondrial
Dysfunction (Membrane Potential)

| | Fluorescence Intensity Ratio (Red/Green) |
|---|---|
| Control Group (n = 5) | 1.00 ± 0.07 |
| JCM Bacterial Cell-Administered Group (n = 5) | 1.78 ± 0.30 |

Each value is the average ± standard error.

[Test Example 7] Examination of Improvement Effect on Mitochondrial Dysfunction (1) Nematode Culture and Preparation of Test Plates The nematode culture and the preparation of test plates were conducted in the same manners as those in Test Example 4 (1). In this regard, however, the bacterial cells smeared on the test product plates were the ATCC bacterial cells or the JCM bacterial cells.

Moreover, bacterial cells of OP50 which were cultured/collected in the same manners as those in Test Example 4 (1) were added to S-complete medium (bacterial cells 6 mg/mL).

(2) Induction of Mitochondrial Dysfunction and Measurement of ROS Production Amount Nematodes which were cultured for three days on the control plates or the test product plates were suspended in the bacterial cell-comprising S-complete medium prepared above and cultured for six hours after adding mitochondrial dysfunctional reagent paraquat (final concentration: 1 mM) and H2DCFDA (a final concentration of 500 μM). Then, the production amounts of reactive oxygen species (ROS) were quantified by measuring the fluorescence intensities (Ex: 480 nm/Em: 530 nm) using a plate reader, and the nematode number in each well was counted under a microscope and used for correction.

(3) Results

The ROS production amounts in the nematodes in which mitochondrial dysfunction was induced by paraquat treatment are shown in Table 7. The ROS production was suppressed by the administration of the ATCC bacterial cells or the JCM bacterial cells. Specifically, while ROS were produced also in the nematodes under the normal conditions without paraquat treatment, the production was suppressed to 0.014 times the amount of the control by the administration of the ATCC bacterial cells and to 0.034 times the amount by the administration of the JCM bacterial cells. Moreover, in the nematodes in which mitochondrial dysfunction was induced by paraquat treatment, the ROS production was suppressed to 0.008 times the amount of the control by the administration of the ATCC bacterial cells and to 0.024 times the amount by the administration of the JCM bacterial cells.

TABLE 7

Improvement Effect on ROS Production in Mitochondrial
Dysfunction-Induced Nematodes

| | Normal Conditions (Without Paraquat Treatment) | Mitochondrial Dysfunction Induction (With Paraquat Treatment) |
|---|---|---|
| Control Group | 15,247 | 137,155 |
| ATCC Bacterial Cell-Administered Group | 220 | 1,068 |
| JCM Bacterial Cell-Administered Group | 518 | 3,339 |

Each value is the fluorescence intensity/number of individuals.

[Test Example 8] Examination of Lifespan-Prolonging Effect in Nematodes (1) Nematode Culture The nematode culture and the culture/collection of OP50 as the feed for the nematodes were conducted in the same manners as those in Test Example 4 (1).

(2) Assessment Method of Lifespan

Synchronized nematodes (L4/adult stage) were cultured in 2'-deoxy-5-fluorouridine-comprising S-complete medium. In this regard, 2'-deoxy-5-fluorouridine was added to prevent hatching of new individuals. Normal OP50 feed was given to the control group (bacterial cells 6 mg/mL). Feed obtained by replacing a half of the amount of normal OP50 feed with the ATCC bacterial cells was given to the ATCC bacterial cell-administered group, and feed obtained by replacing a half of the amount of normal OP50 feed with the JCM bacterial cells was given to the JCM bacterial cell-administered group. The numbers of living individuals were counted using a microscope every two to three days. The survival curves were calculated from the obtained data using the Kaplan-Meier method.

(3) Results

The survival curves (lifespan) in which the third day after hatching (L4/adult stage) was considered as day 0 are shown in FIG. 1. A significant lifespan-prolonging effect was observed in the ATCC bacterial cell-administered group and the JCM bacterial cell-administered group. Specifically, while the average lifespan (days) of the control group was 15.5±1.38, that of the JCM bacterial cell-administered group was 23.2±0.62, and that of the ATCC bacterial cell-administered group was 23.8±0.86.

The invention claimed is:

1. A method of improving mitochondrial function in a subject comprising administering an *Akkermansia muciniphila* bacterium, a culture of the bacterium, or a treated product of the bacterium to the subject, wherein as a result of the administering, the subject has suppressed muscle inflammation.

2. The method according to claim 1, wherein the bacterium is administered in a form of a food or a drink.

3. The method according to claim 1, wherein the bacterium is administered in a form of a pharmaceutical product.

4. The method according to claim 1, wherein the bacterium is crushed, heated or lyophilized bacterial cells or culture of the bacterium, a diluted product thereof, a dried product thereof, or a fraction thereof.

5. The method according to claim 1, wherein the bacterium is administered at a dosage of 0.5 g/day to 5 g/day.

6. The method according to claim 1, wherein the bacterium is administered at a dosage of $1 \times 10^4$ cells/g to $1 \times 10^{13}$ cells/g.

7. The method according to claim 1, wherein the bacterium is selected from the group consisting of *Akkermansia muciniphila* strain JCM30893, and/or *Akkermansia muciniphila* strain ATCC BAA-835, and combinations thereof.

8. The method according to claim 1, wherein said administering is an oral route.

9. The method according to claim 1, wherein said administering is an oral parenteral route.

* * * * *